United States Patent [19]

Martel et al.

[11] 4,277,617
[45] Jul. 7, 1981

[54] PROCESS FOR THE PREPARATION OF ESTERS

[75] Inventors: Jacques Martel, Bondy; Jean Tessier, Vincennes; Jean-Pierre Demoute, Montreuil-sous-Bois; André Teche, Nanterre, all of France

[73] Assignee: Roussel Uclaf, Paris, France

[21] Appl. No.: 951,184

[22] Filed: Oct. 13, 1978

[30] Foreign Application Priority Data

| Oct. 27, 1977 [FR] | France | 77 32414 |
| Oct. 27, 1977 [FR] | France | 77 32415 |
| Jul. 24, 1978 [FR] | France | 78 21811 |
| Jul. 24, 1978 [FR] | France | 78 21812 |

[51] Int. Cl.$^3$ ............... C07C 69/74; C07C 69/743
[52] U.S. Cl. ............. 560/124; 260/326 A; 260/347.4; 260/464; 260/465 D; 560/61; 560/105; 424/274; 424/285; 424/304; 424/305
[58] Field of Search ............... 560/124; 424/305, 304; 260/465 D

[56] References Cited

U.S. PATENT DOCUMENTS

| 3,666,789 | 5/1972 | Itaya et al. | 424/305 X |
| 3,683,005 | 8/1972 | Sota et al. | 424/305 X |
| 3,835,176 | 9/1974 | Matsuo et al. | 260/465 D |
| 3,981,903 | 9/1976 | Hirano et al. | 560/124 |
| 4,127,728 | 11/1978 | Schmidt et al. | 260/465 D X |
| 4,152,455 | 5/1979 | Engel | 424/305 |

FOREIGN PATENT DOCUMENTS 7409256  1/1975  Netherlands ............... 560/124

OTHER PUBLICATIONS

Royals, "Advanced Organic Chemistry", 1954, p. 608.
French, et al., J.A.C.S., 43(1921), pp. 651-659.

Primary Examiner—Joseph Paul Brust
Attorney, Agent, or Firm—Hammond & Littell, Weissenberger and Muserlian

[57] ABSTRACT

Novel esters in the form of their stereoisomers and mixtures of stereoisomers of the formula

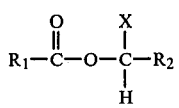

wherein X is selected from the group consisting of fluorine, chlorine and bromine $R_1$ is selected from the group consisting of

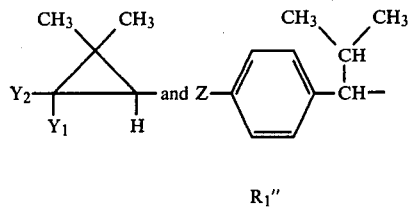

$Y_1$ and $Y_2$ may both be methyl and when $Y_1$ is hydrogen, $Y_2$ is selected from the group consisting of

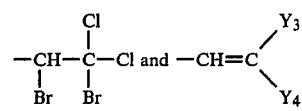

and $Y_3$ and $Y_4$ are individually selected from the group consisting of fluorine, bromine and chlorine or the group consisting of hydrogen and methyl, Z is selected from the group consisting of hydrogen, fluorine, chlorine, bromine, alkyl of 1 to 4 carbon atoms and alkoxy of 1 to 4 carbon atoms, and when $Y_2$ is

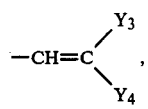

$R_2$ is selected from the group consisting of

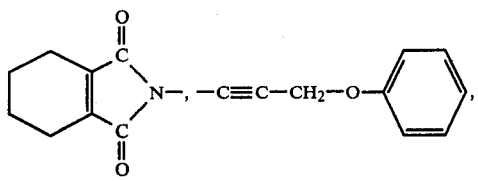

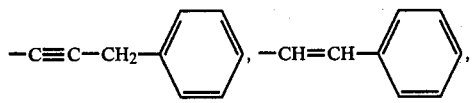

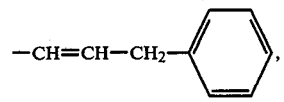

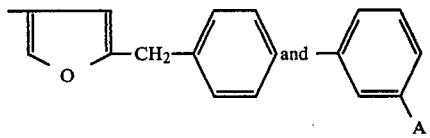

A is selected from the group consisting of

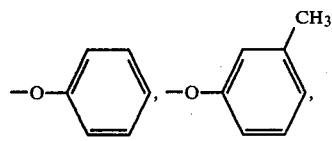

-continued

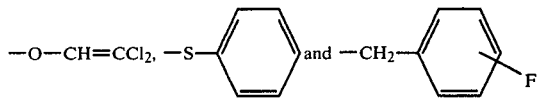

and when $Y_2$ is —CHBr—CCl$_2$Br, $R_2$ is m-phenoxyphenyl and when $R_1$ is $R_1'$ and $Y_2$ is

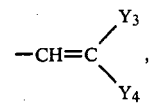

the said acid moiety may be in the cis or trans form or mixtures thereof or optically active isomeric form or racemic mixtures thereof and when $R_1$ is $R_1''$, the said acid moiety is optically active isomeric form or racemic mixtures thereof and the compounds may be in one of two diastereoisomeric forms due to the existence of the asymetrical carbon atoms to which X is attached having insecticidal activity and their preparation.

1 Claim, No Drawings

PROCESS FOR THE PREPARATION OF ESTERS

STATE OF THE ART

French Pat. No. 2,185,612 and an article of Thieme [Synthesis International Journal of Methods in Organic Chemistry No. 9 Sept. 1975] describe similar types of compounds.

OBJECTS OF THE INVENTION

It is an object of the invention to provide the novel esters of formula $I_A$ and a novel process for their preparation.

It is another object of the invention to provide novel insecticidal compositions and a novel method of combatting insects.

These and other objects and advantages of the invention will become obvious from the following detailed description.

THE INVENTION

The novel esters of α-haloalcohols of the invention are comprised of esters in the form of their stereoisomers and mixtures of stereoisomers of the formula

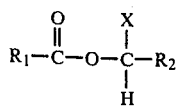

$I_A$ wherein X is selected from the group consisting of fluorine, chlorine and bromine, $R_1$ is selected from the group consisting of

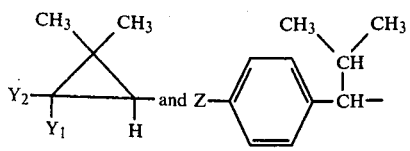

$Y_1$ and $Y_2$ may both be methyl and when $Y_1$ is hydrogen, $Y_2$ is selected from the group consisting of

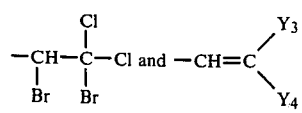

are individually selected from the group consisting of fluorine, bromine and chlorine or the group consisting of hydrogen and methyl, Z is selected from the group consisting of hydrogen, fluorine, chlorine, bromine, alkyl of 1 to 4 carbon atoms and alkoxy of 1 to 4 carbon atoms, and when $Y_2$ is

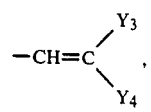

$R_2$ is selected from the group consisting of

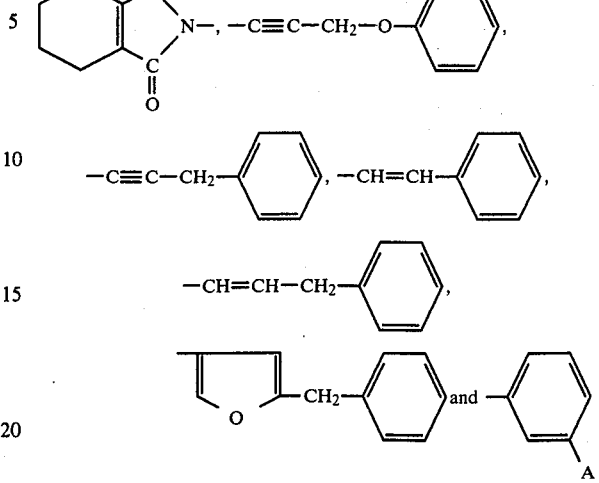

A is selected from the group consisting of

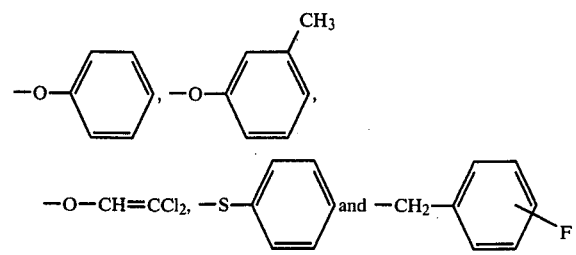

and when $Y_2$ is —CHBr—CCl$_2$Br, $R_2$ is m-phenoxyphenyl and when $R_1$ is $R_1'$ and $Y_2$ is

the said acid moiety may be in the cis or trans form or mixtures thereof or optically active isomeric form or racemic mixtures thereof and when $R_1$ is $R_1'''$, the said acid moiety is optically active isomeric form or racemic mixtures thereof and the compounds may be in one of two diastereoisomeric forms due to the existence of the asymetrical carbon atoms to which X is attached.

Among the compounds of formula $I_A$ are the stereoisomers of compounds of the formula

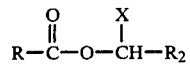

I wherein $R_2$ and X have the above definition and R is selected from the group consisting of $R_1'''$, as defined above and

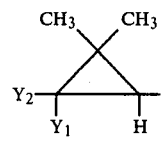

wherein $Y_1$ and $Y_2$ are both methyl or $Y_1$ is hydrogen and $Y_2$ is

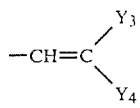

and $Y_3$ and $Y_4$ are individually selected from the group consisting of fluorine, chlorine and bromine or from the group consisting of hydrogen and methyl, so that when $Y_2$ is not methyl, the acid moiety have cis or trans structure or a mixture thereof or optically active isomers or a racemic mixture.

The compounds of formula $I_A$ may exist in numerous stereoisomeric forms. When $Y_1$ is hydrogen and $Y_2$ is

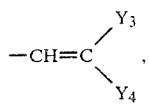

the $R_1$ group possesses asymetric carbon atoms in the 1- and 3-positions of the cyclopropane ring and the corresponding carboxylic acids may have cis or trans structure or mixtures thereof or be optically active isomers or racemates. When $Y_3$ and $Y_4$ are different, there further exists an (E) and (Z) isomer about the double bond.

When $R_1''$ is derived from 2-aryl-2-isopropylacetic acids substituted on the 2-carbon atoms, the 2-carbon atom is asymetrical which causes the existence of 2 enantiomeric forms or a racemate. In addition, the carbon of the compounds of formula $I_A$ carrying the X substituted is an asymetric carbon.

It is considered as probable that after the process to prepare the compounds of formula $I_A$, wherein $R_1$ contains one or more asymetrical carbon atoms of absolute well defined configuration, there is an asymetric induction on the carbon atoms carrying the X substituent. However, the said induction obtained is not, in general, total and the central chiral (carrying the X) is not, in general, entirely the (R) structure and not entirely the (S) structure with the results that the product of formula $I_A$ is a mixture of 2 diastereoisomers which may be separated into the isomer A and isomer B.

By convention, isomer A is the isomer which is more mobile in thin layer chromatography. According to certain theoretical considerations but without being limited to the exactness of the assignment of chirality which has been deduced, it is plausible to attribute to the A isomer the absolute (S) configuration for the carbon substituted with X.

The asymetric carbon atoms of the ethyl side chain of compounds of formula $I_A$ where $R_1$ is the group in which $Y_1$ is hydrogen and $Y_2$ is

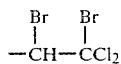

has for its part the existence of 2 diastereoisomers which can be separated by chromatography, for example.

The compounds of formula $I_A$ encompass with the definitions for X, $R_1$ and $R_2$ all the compounds arising from the combination an optically active isomer or racemate resulting from the existence of asymetric carbons of the acid $R_1$ moiety of the molecule with an optically active isomer or racemate of the alcohol moiety

The preferred compounds of formula $I_A$ include those wherein $R'$ has the definition in which $Y_1$ is hydrogen and $Y_2$ is
and those wherein $R_2$ is

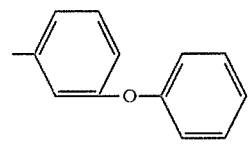

those wherein X is fluorine, those wherein $R_2$ is

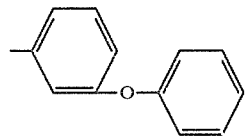

and X is fluorine, bromine or chlorine.

Examples of specific preferred compounds of formula $I_A$ are RS α-chloro-3-phenoxy-benzyl 1R, cis 2,2-dimethyl-3-(2',2'-dibromovinyl)-cyclopropane-1-carboxylate, RS α-fluoro-3-phenoxy-benzyl 1R, cis 2,2-dimethyl-3-(2',2'-dibromovinyl)-cyclopropane-1-carboxylate, RS α-chloro-3-phenoxy-benzyl 1R, cis 2,2-dimethyl-3-(2',2'-dichlorovinyl)cyclopropane-1-carboxylate, RS α-chloro-3-phenoxy-benzyl 2-(p-chlorophenyl)-2-isopropyl-acetate and RS α-chloro-3-phenoxybenzyl 1R, trans 2,2-dimethyl-3-(1',2'-dibromo-2',2'-dichloroethyl)-cyclopropane-1-carboxylate.

The novel process of the invention for the preparation of the compounds of formula $I_A$ comprises reacting an acid halide of the formula

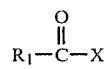

when X and $R_1$ have the above definitions with an aldehyde of the formula

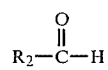

wherein $R_2$ has the above definition in the presence of an acid catalyst to form the compound of formula $I_A$. To produce the compounds of formula I, the acid halide may have the formula

wherein R and X have the above definitions.

The acid bromides and chlorides of formulae II and $II_A$ may be effected by classical methods and the fluorides of the said acids are advantageously prepared by the process of Mukaiyama, Chem. Letters (1976), p. 303–306. The acid catalyst used in the condensation reaction is preferably a Lewis acid such as zinc chloride, aluminum chloride or ferric chloride or a protonic acid such as p-toluene sulfonic acid or oleum. The condensation may be effected by simply mixing the reactants and the acid catalyst without a solvent but the presence of an organic solvent is equally useful.

A preferred embodiment of the process to produce compounds of formula I wherein X is fluorine and $R_2$ is selected from the group consisting of

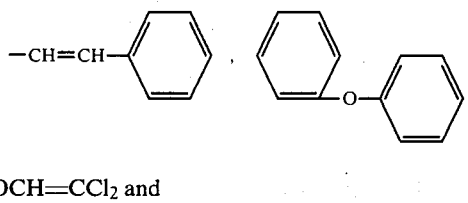

—OCH=CCl$_2$ and

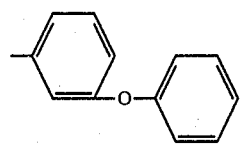

comprises reacting a quaternary ammonium fluoride fixed on a resin with a ($Z_1$) having a formula selected from the group consisting of

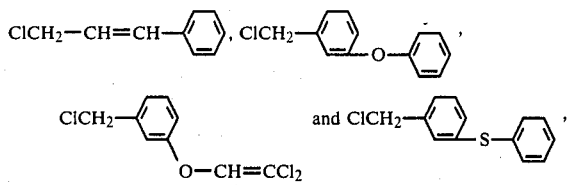

subjecting the corresponding fluoride ($Z_2$) to the action of N-bromosuccinimide in the presence of azoisobutyronitrile to obtain a mixed bromide and fluoride derivative $Z_3$ of the formula

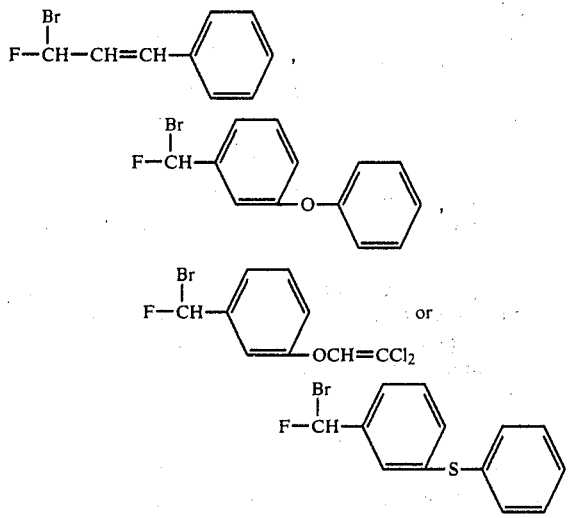

and reacting the latter with an alkali metal salt of the formula

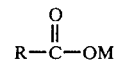

$$R-\overset{O}{\underset{\|}{C}}-OM \quad IV$$

wherein R has the above definition and M is an alkali metal ion.

For the preparation of the fluoride ($Z_2$), a resin of the Amberlite A-26 type is advantageously used which is washed by percolation with an aqueous sodium hydroxide solution and then water washed until the wash water is neutral and the resulting wet resin is stirred with an aqueous hydrofluoric acid solution and is then washed with water and dried by washing with organic solvents. The fluorination of the chloride ($Z_1$) with the said resin is advantageously effected in an organic solvent such as toluene.

The reaction of the fluoride ($Z_2$) and N-bromosuccinimide in the presence of azoisobutyronitrile is conveniently effected in refluxing carbon tetrachloride. The condensation of the mixed bromide-fluoride ($Z_3$) with the salt of formula II is preferably effected in an organic solvent such as dimethylformamide.

The novel insecticidal compositions of the invention are comprised of an insecticidally effective amount of at least one compound of formula I and a carrier. The compositions contain 0.01 to 95%, preferably 0.05 to 10%, by weight of the active products. The compositions preferably contain a synergist such as piperonyl butoxide or N-(2-ethylheptyl)-bicyclo (2,2,1)-5-hepten-2,3-dicarboxiimide and may contain one or more other pesticidal agents. The compositions may be in the form of powders, granules, suspensions, emulsions, solutions, aerosol compositions, combustible tapes, coils, or other classically used preparations for the use of compounds of this nature and are useful in the home and agriculture. The preferred compounds of formula $I_A$ are those wherein $R_2$ is Examples of the inert carriers of the compositions of the invention are a vehicle and/or a nonionic surface active agent to ensure a uniform dispersion of the substance making up the composition. The vehicle may be a liquid such as water, alcohol, hydrocarbons, other organic solvents, or a mineral, animal or vegetable oil or a powdered solid such as talc, clays, silicates, kieselguhr or a combustible solid such as tabu powder (or pyrethrum residue).

The novel insecticidal method of the invention comprises contacting insects with a lethal dose of at least one compound of formula $I_A$.

The compounds of formula $I_A$ are also useful intermediates for the synthesis of esters possessing remarkable insecticidal properties and it is a further object of the invention to provide a process for the preparation of compounds in stereoisomeric form or mixtures thereof of the formula

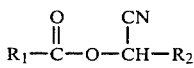

wherein $R_1$ and $R_2$ have the same definitions as in formula $I_A$ with it being well understood that the existence of the asymetrical carbon atom carrying the $CN^-$ carries over into the obtained ester with the stereoisomeric acid defined in a unique fashion, the existence of 2 diastereoisomers (isomers A and B). The process comprises reacting a compound which generates $CN^-$ ions with a compound of formula $I_A$ to obtain the corresponding compound of formula $I_B$ existing in the stereoisomeric forms corresponding to the starting compound of formula $I_A$. The compounds of formula I may be used in place of the compounds of formula $I_A$ and the compounds of the formula

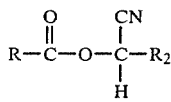

wherein R and $R_2$ have the above definition, are thus obtained

Preferably, X is chlorine or fluorine and the condensation reaction is effected in an anhydrous organic solvent selected from the group consisting of acetonitrile and dimethylformamide. The compound generating $CN^-$ ions is preferably an alkali metal cyanide such as potassium cyanide or sodium cyanide but equally useful are other cyanide ion generators such as tetraethylammonium cyanide, 1-methyl-1-ethyl-ethanolnitrile and cuprous cyanide. The isomeric mixtures may be separated by known methods.

The process of the invention for the preparation of compounds of $I_B$ or $I_C$ is particularly useful for preparing RS α-cyano-3-phenoxy-benzyl 1R, cis 2,2-dimethyl-3-(2′,2′-dibromovinyl)-cyclopropane-1-carboxylate starting from RS α-chloro-3-phenoxy-benzyl 1R, cis 2,2-dimethyl-3-(2′,2′-dibromovinyl)-cyclopropane-1-carboxylate; RS α-cyano-3-phenoxy-benzyl 1R, cis, 2,2-dimethyl-3-(2′,2′-dibromovinyl)-cyclopropane-1-carboxylate starting from RS α-fluoro-3-phenoxybenzyl 1R, cis 2,2-dimethyl-3-(2′,2′-dibromovinyl)-cyclopropane-1-carboxylate; RS α-cyano-3-phenoxy-benzyl 1R, cis 2,2-dimethyl-3-(2′,2′-dichlorovinyl)-cyclopropane-1-carboxylate starting from RS α-chloro-3-phenoxy-benzyl 1R, cis 2,2-dimethyl-3-(2′,2′-dichlorovinyl)-cyclopropane-1-carboxylate; RS α-cyano-3-phenoxy-benzyl 2-(p-chlorophenyl)-2-isopropylacetate starting from RS α-chloro-3-phenoxy-benzyl 2-(p-chlorophenyl)-2-isopropyl-acetate; and RS α-cyano-3-phenoxy-benzyl 1R, trans 2,2-dimethyl-3-(1′,2′-dibromo-2′,2′-dichloroethyl)cyclopropane-1-carboxylate starting from RS α-chloro or fluoro-3-phenoxy-benzyl 1R, trans 2,2-dimethyl-3-(1′,2′-dibromo-2′,2′-dichloroethyl)-cyclopropane-1-carboxylate.

The many compounds of formula $I_B$ are well known for their intense insecticidal activity such as French Pat. No. 2,185,612 and published French application Ser. No. 2,364,884. Especially useful are RS α-cyano-3-phenoxy-benzyl 1R cis 2,2-dimethyl-3-(2′,2′-dibromovinyl)-cyclopropane-1-carboxylate, RS α-cyano-3-phenoxy-benzyl 1R, cis 2,2-dimethyl-3-(2′,2′-dichlorovinyl)-cyclopropane-1-carboxylate and RS α-cyano-3-phenoxy-benzyl 1R, trans 2,2-dimethyl-3-(1′,2′-dibromo-2′,2′-dichloroethyl)-cyclopropane-1-carboxylate.

The process of the invention for the preparation of the compounds of formula $I_A$ as well as the process for the compounds of formula $I_B$ is a new economical process for access to the compounds of formula $I_B$ with the advantages of readily accessible reactants leading to high yields of the compounds of formula $I_B$ while avoiding the use of α-cyano-3-phenoxy-benzyl alcohol which is a fragile and delicate compound to handle.

The compounds of formula II are known compounds and among these the acid chlorides of the formula

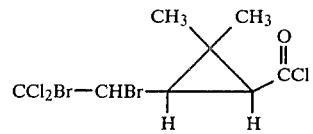

are described in French Pat. No. 2,364,884 which also permits the preparation of the corresponding acids. The other acid halides can be prepared by classical methods starting from the corresponding acids of French Pat. No. 2,364,884.

In the following examples there are described several preferred embodiments to illustrate the invention. However, it is to be understood that the invention is not intended to be limited to the specific embodiments.

EXAMPLE 1

RS α-chloro-3-phenoxy-benzyl 1R, cis 2,2-dimethyl-3-(2′,2′-dibromovinyl)-cyclopropane-1-carboxylate 10 mg of fused zinc chloride in the form of a powder were added to a mixture of 6.4 g of 1R, cis 2,2-dimethyl-3-(2′,2′-dibromovinyl)-cyclopropane-1-carboxylic acid [prepared by process of Example 16 of French Pat. No. 2,185,612] and 4 g of m-phenoxy-benzaldehyde and heating and thickening of the medium was noted. The mixture stood for one hour at 20° C. under strict anhydrous conditions to obtain RS α-chloro-3-phenoxy-benzyl 1R, cis 2,2-dimethyl-3-(2′,2′-dibromovinyl)-cyclopropane-1-carboxylate.

IR Spectrum (chloroform): Absorption at 1749 cm$^{-1}$ (C=O)

RMN Spectrum (deuterochloroform): Peaks at 1.26–1.33 ppm (hydrogens of geminal methyls); at 1.85–2.10 ppm (hydrogens of cyclopropyl); at 6.76–6.90 ppm (ethylenic hydrogen); at 7.0 ppm and 7.66 ppm (hydrogens of aromatic ring and benzyl).

EXAMPLE 2

RS α-chloro-3-phenoxy-benzyl 1R, cis 2,2-dimethyl-3-(2′,2′-dibromovinyl)-cyclopropane-1-carboxylate Using the procedure of Example 1 with 60 mg of ferric chloride and stirring for 4 hours, raw RS α-chloro-3-phenoxy-benzyl 1R, cis 2,2-dimethyl-3-(2′,2′-dibromovinyl)-cyclopropane-1-carboxylate was obtained.

EXAMPLE 3

Using the procedure of Example 1 with 60 mg of p-toluene sulfonic acid and stirring for 20 hours, raw RS α-chloro-3-phenoxy-benzyl 1R, cis 2,2-dimethyl-3-(2′,2′-dibromovinyl)-cyclopropane-1-carboxylate was obtained.

EXAMPLE 4

Using the procedure of Example 1 with a drop of 65% oleum and stirring for one hour, raw RS α-chloro-3-phenoxy-benzyl 1R, cis 2,2-dimethyl-3-(2',2'-dibromovinyl)-cyclopropane-1-carboxylate was obtained.

EXAMPLE 5

RS α-bromo-3-phenoxy-benzyl 1R, cis 2,2-dimethyl-3-(2',2'-dibromovinyl)-cyclopropane-1-carboxylate

Step A: 1R, cis 2,2-dimethyl-3-(2',2'-dibromovinyl)-cyclopropane-1-carboxylic acid bromide 0.2 ml of pyridine were added to a solution of 18 g of 1R, cis 2,2-dimethyl-3-(2',2'-dibromovinyl)-cyclopropane-1-carboxylic acid in 60 ml of toluene and then 6 ml of phosphorus tribromide were progressively added thereto. The mixture was stirred at 20° C. for 6 days and was then decanted to separate a dense oil in the lower phase of the reaction mixture. The solvent was distilled under reduced pressure and the residue was rectified to obtain 14 g of 1R, cis 2,2-dimethyl-3-(2',2'-dibromovinyl)-cyclopropane-1-carboxylic acid bromide with a boiling point of 110° C. at 0.2 mm Hg.

IR Spectrum (chloroform): Absorption at 1792 cm$^{-1}$ (COOH).

RMN Spectrum (deuterochloroform): Peaks at 1.32–1.36 ppm (hydrogens of geminal methyls); at 2.12–2.26–2.40 ppm (1-hydrogen of cyclopropyl); at 2.66–2.80 ppm (3-hydrogen of cyclopropyl); at 6.53–6.66 ppm (ethylenic hydrogen).

Step B: RS α-bromo-3-phenoxy-benzyl 1R, cis 2,2-dimethyl-3-(2',2'-dibromovinyl)-cyclopropane-1-carboxylate 5 mg of zinc chloride were added to a mixture of 5.66 g of the product of Step A and 3.11 g of m-phenoxybenzaldehyde after which heat and a thickening of the mixture was noted. The mixture stood for 1 hour at 20° C. under strictly anhydrous conditions to obtain RS α-bromo-3-phenoxybenzyl 1R, cis 2,2-dimethyl-3-(2',2'-dibromovinyl)-cyclopropane-1-carboxylate.

IR Spectrum (chloroform): Absorption at 1750 cm$^{-1}$ (COOH).

RMN Spectrum (deuterochloroform): Peaks at 1.26–1.33 ppm (hydrogens of geminal methyls); at 1.75–2.16 ppm (hydrogens of cyclopropyl); 6.76–6.88 ppm (ethylenic hydrogen); 7.0–7.75 ppm (hydrogens of phenyl and benzyl).

EXAMPLE 6

RS α-chloro-3-phenoxy-benzyl 1R, trans 2,2-dimethyl-3-(2',2'-dibromovinyl)-cyclopropane-1-carboxylate 10 mg of zinc chloride were added to a mixture of 6.4 g of 1R, trans 2,2-dimethyl-3-(2',2'-dibromovinyl)-cyclopropane-1-carboxylic acid chloride and 4 g of m-phenoxy-benzaldehyde and the mixture was stirred for one hour to obtain a solution of RS α-chloro-3-phenoxy-benzyl 1R, trans 2,2-dimethyl-3-(2',2'-dibromovinyl)-cyclopropane-1-carboxylate.

EXAMPLE 7

RS α-chloro-3-phenoxy-benzyl 1R, cis 2,2-dimethyl-3-(2',2'-dichlorovinyl)-cyclopropane-1-carboxylate 10 mg of zinc chloride were added to a mixture of 4.6 g of 1R, cis 2,2-dimethyl-3-(2',2'-dichlorovinyl)-cyclopropane-1-carboxylic acid chloride and 4 g of m-phenoxy-benzaldehyde and the mixture was stirred for one hour to obtain a solution of RS α-chloro-3-phenoxy-benzyl 1R, cis 2,2-dimethyl-3-(2',2'-dichlorovinyl)-cyclopropane-1-caboxylate.

EXAMPLE 8

RS α-chloro-3-phenoxy-benzyl 2,2-dimethyl-3R-(2'-methyl-1'-propenyl)-cyclopropane-1R-carboxylate 10 mg of zinc chloride were added to a mixture of 1.89 g of 2,2-dimethyl-3R-(2'-methyl-1'-propenyl)-cyclopropane-1R-carboxylic acid chloride and 2 g of m-phenoxy-benzaldehyde and the mixture was stirred for 2½ hours to obtain 3.89 g of raw RS α-chloro-3-phenoxy-benzyl 2,2-dimethyl-3R-(2'-methyl-1'-propenyl)-cyclopropane-1R-carboxylate.

EXAMPLE 9

RS α-chloro-3-phenoxy-benzyl 2-(p-chlorophenyl)-2-isopropylacetate 10 mg of zinc chloride were added to a mixture of 4.7 g of 2-(p-chlorophenyl)-2-isopropyl-acetyl chloride and 4 g of m-phenoxy-benzaldehyde and the mixture was stirred for 3 hours at 20° C. to obtain a solution of RS α-chloro-3-phenoxybenzyl 2-(p-chlorophenyl)-2-isopropyl-acetate.

EXAMPLE 10

RS α-chlorocinnamyl 1R, cis 2,2-dimethyl-3-(2',2'-dibromovinyl)-cyclopropane-1-carboxylate 10 mg of zinc chloride were added to a mixture of 4.84 g of 1R, cis 2,2-dimethyl-3-(2',2'-dibromovinyl)-cyclopropane-1-carboxylic acid chloride and 2.22 g of cinnamic aldehyde and the mixture was stirred for one hour at 20° C. to obtain 7.06 g of raw RS α-chlorocinnamyl 1R, cis 2,2-dimethyl-3-(2',2'-dibromovinyl)-cyclopropane-1-carboxylate melting at about 82° C.

EXAMPLE 11

RS α-fluoro-3-phenoxy-benzyl 1R, cis 2,2-dimethyl-3-(2',2'-dibromovinyl)-cyclopropane-1-carboxylate

Step A: m-phenoxy-benzyl fluoride

Using the procedure of Cainelli et al [Synthesis, 1976, p. 472], 220 g of Amberlite A-26 resin was washed by percolation with 1.5 liters of N aqueous sodium hydroxide and then with water until the wash water was neutral. The wet resin containing OH$^-$ groups was stirred for 20 hours at 20° C. in an aqueous N hydrofluoric acid solution and was then vacuum filtered. The resin was washed with water, acetone and then ether and was dried at 50° C. under reduced pressure for 10 hours.

A mixture of 40 g of the said resin, 10.5 g of m-phenoxy benzyl chloride and 150 ml of toluene was heated with stirring at 100° C. for 20 hours and was then filtered to remove the resin. The filter was washed with methylene chloride and the filtrate was evaporated to dryness under reduced pressure. The residue was rectified to obtain 5.8 g of m-phenoxy-benzyl fluoride boiling at 93° C. at 0.05 mm Hg.

RMN Spectrum (deuterochloroform): Peaks at 4.91–5.71 ppm (hydrogens of —CH$_2$F); at 6.91–7.6 ppm (hydrogens of aromatic ring).

Step B: 1-bromofluoromethyl-3-phenoxy-benzene

A mixture of 2 g of the product of Step A, 2 g of N-bromosuccinimide, 50 g of azoisobutyronitrile and 20 ml of carbon tetrachloride was refluxed for one hour and was then cooled and filtered. The filtrate was evaporated to dryness under reduced pressure and the residue was chromatographed over silica gel. Elution with petroleum ether (b.p.=35°–75° C.) yielded 1.8 g of 1-bromofluoromethyl-3-phenoxybenzene.

Analysis: Calculated: %C 55.54; %H 3.58; %Br 28.42; %F 6.75; Found: %C 56.1; %H 3.7; %Br 28.0; %F 6.4.

RMN Spectrum (deuterochloroform): Peaks at 6.43–7.75 ppm (hydrogen of —CHBrF); at 6.91–7.5 ppm (hydrogens of aromatic ring).

Step C: RS α-fluoro-3-phenoxy-benzyl 1R, cis 2,2-dimethyl-3-(2′,2′-dibromovinyl)-cyclopropane-1-carboxylate A mixture of 1.19 g of the product of Step B, 1.5 g of sodium 1R, cis 2,2-dimethyl-3-(2′,2′-dibromovinyl)-cyclopropane-1-carboxylate and 10 ml of dimethylformamide was stirred at 20° C. for 17 hours and was then poured into a water-ice mixture. The mixture was extracted with benzene and after the usual treatment, the benzene extract was evaporated to dryness under reduced pressure. The raw residue was a mixture of 2-diastereoisomers of RS α-fluoro-3-phenoxybenzyl 1R, cis 2,2-dimethyl-3-(2′,2′-dibromovinyl)-cyclopropane-1-carboxylate and was subjected to chromatography over silica gel. Elution with a 95–5 petroleum ether (b.p.=35°–75° C.)-ether mixture yielded 0.530 g of the diastereisomer A melting at 80° C. (more mobile) and 0.700 g of diastereoisomer B melting at 50° C. (less mobile) as well as 0.420 g of a mixture of the 2 isomers for a total yield of 1.65 g of the desired ester.

RMN Spectrum (deuterochloroform): isomer A: Peaks at 1.32–1.35 ppm (hydrogens of geminal methyls); 6.8–7.71 ppm (hydrogen of carbon attached to fluorine); at 1.85–2.1 ppm (hydrogens of cyclopropyl); at 6.66–7.83 ppm (hydrogens of aromatic ring).

Circular dichroism (dioxane): isomer A: $\Delta\epsilon = +0.30$ at 284 nm (maximum); $\Delta\epsilon = +0.25$ at 278 nm (maximum); $\Delta\epsilon = +10.8$ at 215 nm (maximum).

RMN Spectrum (deuterochloroform): isomer B: Peaks at 1.28 ppm (hydrogens of geminal methyls); 6.8–7.7 ppm (hydrogen of carbon attached to fluorine); 1.86–2.25 ppm (hydrogens of cyclopropyl); 6.8–7.6 ppm (hydrogens of aromatic ring).

Circular dichroism (dioxane): isomer B: $\Delta\epsilon = -0.77$ at 277 nm (maximum); $\Delta\epsilon = -12.5$ at 227 nm (maximum); $\Delta\epsilon = +7.23$ at 207 nm (maximum).

The same compound was also prepared by reacting 1R, cis 2,2-dimethyl-3-(2′,2′-dibromovinyl)-cyclopropane-1carboxylic acid fluoride and m-phenoxy-benzaldehyde in the presence of zinc chloride.

EXAMPLE 12

RS α-chloro-3-phenoxy-benzyl 1R, trans 2,2-dimethyl-3-(1′,2′-dibromo-2′,2′-dichloroethyl)-cyclopropane-1-carboxylate A mixture of 8 g of 3-phenoxy-benzaldehyde and 15.5 g of 1R, trans 2,2-dimethyl-3-(1′,2′-dibromo-2′,2′-dichloroethyl)-cyclopropane-1-carboxylic acid chloride was warmed to obtain a homogeneous liquid and the mixture was cooled to 20° C. 0.150 g of anhydrous zinc chloride were added thereto and the mixture was stirred at 20° C. for 17 hours to obtain raw RS α-chloro-3-phenoxy-benzyl 1R, trans 2,2-dimethyl-3-(1′,2′-dibromo-2′,2′-dichloroethyl)-cyclopropane-1-carboxylate whose IR spectrum showed an absorption at 1750 cm$^{-1}$ (carbonyl) and whose RMN Spectrum showed the absence of an aldehydic proton.

EXAMPLE 13

RS α-cyano-3-phenoxy-benzyl 1R, cis 2,2-dimethyl-3-(2′,2′-dibromovinyl)-cyclopropane-1-carboxylate 0.8 g of anhydrous potassium cyanide was added to a solution of 5.5 g of the raw product of Example 1 in 50 ml of anhydrous acetonitrile and the mixture was stirred at 20° C. for 17 hours. Water was added thereto and the mixture was extracted with benzene. The benzene extracts were treated in the usual manner to obtain 5.6 g of raw product which was chromatographed over silica gel. Elution with a 9-1 petroleum ether (b.p.=35°–75° C.)-ether mixture yielded 4.3 g of RS α-cyano-3-phenoxy-benzyl 1R, cis 2,2-dimethyl-3-(2′,2′-dibromovinyl)-cyclopropane-1-carboxylate.

EXAMPLE 14

RS α-cyano-3-phenoxy-benzyl 1R, cis 2,2-dimethyl-3-(2′,2′-dibromovinyl)-cyclopropane-1-carboxylate Using the procedure of Example 13, the α-bromo compound of Example 5 was reacted to obtain RS α-cyano-3-phenoxy-benzyl 1R, cis 2,2-dimethyl-3-(2′,2′-dibromovinyl)cyclopropane-1-carboxylate.

EXAMPLE 15

RS α-cyano-3-phenoxy-benzyl 1R, cis 2,2-dimethyl-3-(2′,2′-dibromovinyl)-cyclopropane-1-carboxylate 0.2 g of potassium cyanide was added to a solution of 1.17 g of the raw α-fluoride compound of Example 11 in 15 ml of acetonitrile and the mixture was stirred at 20° C. for 17 hours. The residue was chromatographed over silica gel and was eluted with a 9-1 petroleum ether-ether mixture to obtain 1 g of RS α-cyano-3-phenoxy-benzyl 1R, cis, 2,2-dimethyl-3-(2′,2′-dibromovinyl)-cyclopropane-1-carboxylate

EXAMPLE 16

RS α-cyano-3-phenoxy-benzyl 1R, trans 2,2-dimethyl-3-(2′,2′-dibromovinyl)-cyclopropane-1-carboxylate 90 ml of acetonitrile were added to the solution obtained in Example 6 and 1.5 g of potassium cyanide were added thereto. The mixture was stirred for 16 hours and water was added thereto after which the mixture was extracted with benzene. The benzene extracts were treated in the usual manner and were evaporated to dryness under reduced pressure. The residue was chromatographed over silica gel and elution with a 6-4 benzene-cyclohexane mixture yielded 7.5 g of RS α-cyano-3-phenoxy-benzyl 1R, trans 2,2-dimethyl-3-(2′,2′-dibromovinyl)-cyclopropane-1-carboxylate.

EXAMPLE 17

RS α-cyano-3-phenoxy-benzyl 1R, cis 2,2-dimethyl-3-(2′,2′-dichlorovinyl)-cyclopropane-1-carboxylate 1.5 g of potassium cyanide were added to a mixture of 80 ml of acetonitrile and the solution of product obtained in Example 7 and the mixture was stirred for 17 hours after which water was added thereto. The mixture was extracted with benzene and the benzene extracts were treated in the usual manner and were evaporated to dryness under reduced pressure. The residue was chromatographed over silica gel and elution with a 6-4 benzene-cyclohexane mixture yieled 6.4 g of RS α-cyano-3-phenoxy-benzyl 1R, cis 2,2-dimethyl-3-(2′,2′-dichlorovinyl)-cyclopropane-1-carboxylate.

EXAMPLE 18

RS α-cyano-3-phenoxy-benzyl 2,2-dimethyl-3R-(2′-methyl-1′-propenyl)-cyclopropane-1R-carboxylate 1.1 g of potassium cyanide were added to a solution of 50 ml of acetonitrile and 3.09 g of the raw product of Example 8 and the mixture was stirred for 48 hours and was poured into ice water. The mixture was extracted with benzene and the benzene extracts were dried over magnesium silicate, filtered and evaporated to dryness under reduced pressure. The 3.96 g of residue was chromatographed over silica gel and was eluted with a 9-1 cyclohexane-ethyl acetate mixture to obtain 0.48 g of RS α-cyano-3-phenoxy-benzyl 2,2-dimethyl-3R-(2′-methyl-1′-propenyl)-cyclopropane-1R-carboxylate.

IR Spectrum (chloroform): Absorption at 1733 cm$^{-1}$ (COOH); at 1487-1587 cm$^{-1}$ (aromatic ring).

EXAMPLE 19

RS α-cyano-3-phenoxy-benzyl 2-(p-chlorophenyl)-2-isopropyl acetate 1.5 g of potassium cyanide were added to a mixture of 80 ml of acetonitrile and the solution obtained in Example 9 and the mixture was stirred at 20° C. for 72 hours. Ether was added to the mixture which was then filtered to remove insolubles. The filtrate was evaporated to dryness under reduced pressure and the residue was chromatographed over silica gel. Elution with a 95-5 cyclohexane-acetone mixture yielded 6.5 g of RS α-cyano-3-phenoxy-benzyl 2-(p-chlorophenyl)-2-isopropyl-acetate.

EXAMPLE 20

RS α-cyano-cinnamyl 1R, cis 2,2-dimethyl-3-(2′,2′-dibromovinyl)-cyclopropane-1-carboxylate 1.5 g of potassium cyanide were added to a mixture of 75 ml of acetonitrile and 4.76 g of the raw product of Example 10 and the mixture was stirred for 42 hours and was poured into ice water. The mixture was extracted with benzene and the benzene extracts were washed with water, dried over magnesium sulfate and filtered. The filtrate was evaporated to dryness under reduced pressure and the 5.3 g of resin was chromatographed over silica gel. Elution with 9-1 cyclohexane-ethyl acetate mixture yielded 1.76 g of RS α-cyano-cinnamyl 1R, cis 2,2-dimethyl-3-(2′,2′-dibromovinyl)-cyclopropane-1-carboxylate.

Analysis: $C_{18}H_{17}Br_2NO_2$; molecular weight=439.16
Calculated: %C 49.2; %H 3.9; %Br 36.4; %N 3.2;
Found: %C 49.5; %H 4.1; %Br 34.2; %N 2.8.

EXAMPLE 21

(S) and (R) α-cyano-3-phenoxy-benzyl esters of 1R, trans 2,2-dimethyl-3-(1′,2′-dibromo-2′,2′-dichloroethyl)-cyclopropane-1-carboxylic acid 17.8 g of the raw product of Example 12 were dissolved in 200 ml of benzene and 2 g of potassium cyanide were added to the solution which then stood at 20° C. for 50 hours with stirring. The mixture was diluted with water and was extracted with benzene. The benzene extracts were evaporated to dryness and the residue was chromatographed over silica gel. Elution with a 1-9 ether-petroleum ether mixture yielded 0.63 g of (R) α-cyano-3-phenoxy-benzyl 1R, trans 2,2-dimethyl-3-(1′,2′-dibromo-2′,2′-dichloroethyl)-cyclopropane-1-carboxylate (compound A) and then 1.13 g of the corresponding (S) α-cyano-3-phenoxy-benzyl ester (compound B).

RMN Spectrum (deuterochloroform): Compound A: Peaks at 1.32-1.35 ppm (hydrogens of 2-methyls of cyclopropyl); at 4.18 and 4.35 ppm and 4.35 and 4.53 ppm (1′-hydrogen of ethyl side chain); at 6.37 ppm (hydrogen on carbon attached to —CN).

RMN Spectrum (deuterochloroform): Compound B: Peaks at 1.2-1.25-1.32 ppm (hydrogens of 2-methyls of cyclopropyl); a 4.21-4.38-4.37-4.53 ppm (1′-proton of ethyl side chain); at 6.42 ppm (benzyl proton).

EXAMPLE 22

An emulsifiable insecticidal concentrate was prepared by intimately admixing 1 g of the A isomer of α-fluoro-3-phenoxy-benzyl 1R, cis 2,2-dimethyl-3-(2′,2′-dibromovinyl)-cyclopropane-1-carboxylate, 20 g of Tween 80 (polyoxyethylene sorbitan mono-oleate), 0.1 g of Topanol A (phenolic antioxidant) and 78.9 g of xylene.

INSECTICIDAL ACTIVITY

The insecticidal activity of the B isomer of α-fluoro-3-phenoxy-benzyl 1R, cis 2,2-dimethyl-3-(2′,2′-dibromovinyl)-cyclopropane-1-carboxylate was determined on house flies. Both sexes of the house fly received a topical application of 1 μl of an acetone solution of the test product on their dorsal thorax. 50 insects were used for each test and the number of dead insects was determined 24 hours after the treatment. One series of tests used the B isomer alone and a second series of tests used a 10-1 piperonyl butoxide-isomer B synergistic mixture. The $DL_{50}$ (dose which killed 50% of the insects) was determined to be 9.2 ng/insect for isomer B alone and 3.13 ng/insect for the synergistic mixture.

Various modifications of the products and processes of the invention may be made without departing from the spirit or scope thereof and it is to be understood that the invention is to be limited only as defined in the appended claims.

We claim:
1. A process for the preparation of a compound of a stereoisomer of a compound of the formula

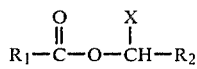

wherein $R_1$ is

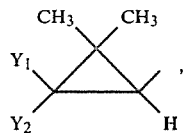

$Y_1$ and $Y_2$ are both methyl or $Y_1$ is hydrogen and $Y_2$ is selected from the group consisting of

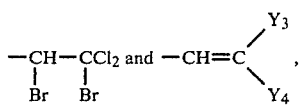

$Y_3$ and $Y_4$ are individually selected from the group consisting of fluorine, chlorine, bromine, hydrogen, and methyl, X is fluorine and $R_2$ is selected from the group consisting of

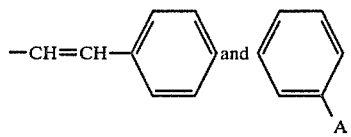

and A is selected from the group consisting of

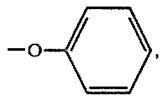

—OCH =CCl$_2$ and

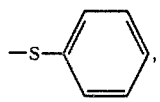

comprising reacting a quaternary ammonium fluoride fixed on a resin with a chloride having a formula selected from the group consisting of

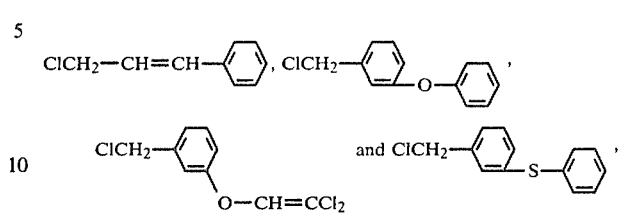

subjecting the corresponding fluoride to the action of N-bromosuccinimide in the presence of azoiosbutyronitrile to obtain a mixed bromide and fluoride derivative of the formula

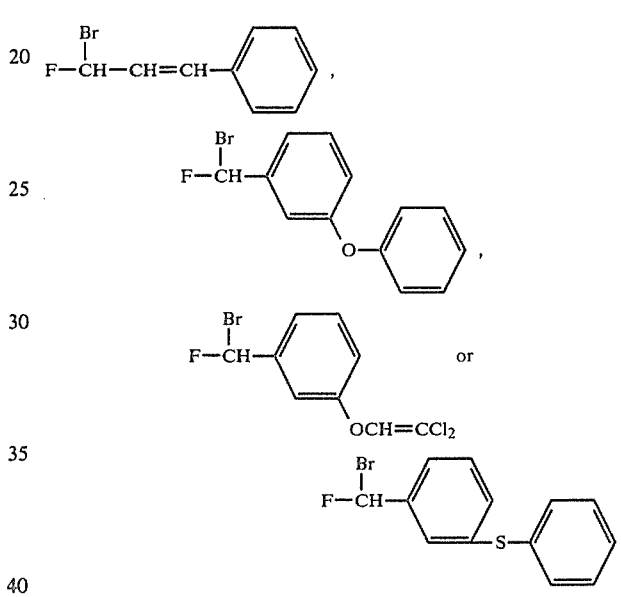

and reacting the latter with an alkali metal salt of the formula

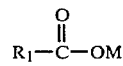

wherein $R_1$ has the above definition and M is an alkali metal ion.

* * * * *

UNITED STATES PATENT AND TRADEMARK OFFICE
CERTIFICATE OF CORRECTION

PATENT NO. : 4,277,617
DATED : July 7, 1981
INVENTOR(S) : JACQUES MARTEL ET AL.

It is certified that error appears in the above—identified patent and that said Letters Patent is hereby corrected as shown below:

Preamble page, [57] Abstract, second column, first structural formula; and
Column 1, line 37, first structural formula: The portion of the structural formula which reads

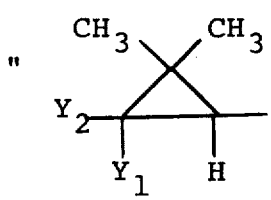  "  should read --  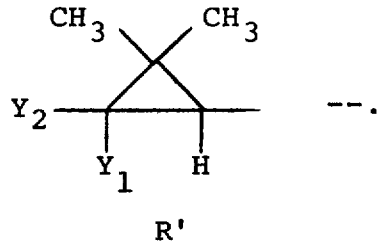  --.

Column 4, line 11: After "$Y_2$ is" insert -- 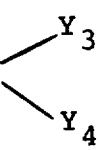 --

Column 11, line 66: "-lcarboxylic" should read -- -1-carboxylic--.

Column 14, line 34: "a 4.21" should read -- at 4.21 --.

Signed and Sealed this

Fifth Day of January 1982

[SEAL]

Attest:

GERALD J. MOSSINGHOFF

*Attesting Officer*  *Commissioner of Patents and Trademarks*